(12) United States Patent
Sarkis et al.

(10) Patent No.: US 7,749,973 B2
(45) Date of Patent: Jul. 6, 2010

(54) METHODS OF GENE TRANSFER TO ASTROCYTES WITH MOKOLA VIRUS PSEUDOTYPED LENTIVIRUS VECTORS

(75) Inventors: Chamsy Sarkis, Paris (FR); Yi He, Paris (FR); Che Serguera, Paris (FR); Noelle Dufour, Mennecy (FR); Jacques Mallet, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 3 days.

(21) Appl. No.: 10/477,375

(22) PCT Filed: May 31, 2002

(86) PCT No.: PCT/FR02/01833

§ 371 (c)(1),
(2), (4) Date: Feb. 12, 2004

(87) PCT Pub. No.: WO02/097104

PCT Pub. Date: Dec. 5, 2002

(65) Prior Publication Data

US 2004/0120929 A1 Jun. 24, 2004

(30) Foreign Application Priority Data

Jun. 1, 2001 (FR) .................... 01 07239

(51) Int. Cl.
*A01N 43/04* (2006.01)
*A01N 65/00* (2006.01)
*A61K 31/70* (2006.01)
*A61K 48/00* (2006.01)
*C12N 15/00* (2006.01)

(52) U.S. Cl. ................. 514/44 R; 424/93.1; 424/93.21; 435/320.1

(58) Field of Classification Search ........................ None
See application file for complete search history.

(56) References Cited

U.S. PATENT DOCUMENTS 6,756,523 B1 6/2004 Kahn et al.

FOREIGN PATENT DOCUMENTS

WO WO 99/61639 12/1999

OTHER PUBLICATIONS

Freed et al. (2001) Fundamental Virology, 4th Ed., "HIVs and Their Replication", Edited by Knipe and Howley, Published by Lippincott, Williams and Wilkins, Baltimore, MD., pp. 913 and 920.*
Rainov, et al. (2001) Curr. Gene Therap., 1: 367-83.*
However, Jacobsen (2002) Curr. Top. Med. Chem., 2(4): 343-52.*
Desmaris, et al. (2001) Molec. Therap., 4(2): 149-56.*
Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Bjorklund, et al. (2000) Brain Research, 886: 82-98.*
Pertusa, et al. (2007) Neurobiology of Aging, [Epublication ahead of print], 14 pages.*
Bizon, et al. (2005) SAGE KE, 7(2): 1-5.*
Potrovita, et al. (2004) J. Neuroscience, 24(38): 8237-44.*
Schuster, et al. (2002) Glia, 40(1): 95-108.*
Pfeifer, et al. (2001) Annu. Rev. Genomics Human. Genet. 2: 177-211.*
Johnson-Saliba, et al. (2001) Curr. Drug. Targets, 2: 371-99.*
Shoji, et al. (2004) Current Pharmaceutical Design, 10: 785-96.*
Kahle, et al. (2001) Emerging Therapeutic Targets, 5(1): 125-32.*
Auricchio et al, "Adeno-associated virus type 5 and pseudotyped-lentiviral vectors as novel gene delivery agents for the retina", IOVS, vol. 42, No. 1, Mar. 15, 2001, p. S125 & Annual Meeting of the Association for Research in Vision and Opthalmology; Fort Lauderdale, Florida, Apr. 29-May 4, 2001.
Mitrophanous et al, "Stable Gene Transfer to the Nervous System Using a Non-Primate Lentiviral Vector", Gene Therapy, MacMillan Press LTD., Basingstoke, GB, vol. 6, No. 11, 1999. pp. 1808-1818.
Mochizuki et al, "High-Titer Human Immunodeficiency Virus Type 1-Based Vector Systems for Gene Delivery into Nondividing Cells", Journal of Virology, vol. 72, No. 11, Nov. 1998, pp. 8873-8883.
Zennou et al, "The HIV-1 DNA flap stimulates HIV vector-mediated cell transduction in the brain", Nat Biotechnol., May 2001, 19(5), pp. 446-450.
Desmaris et al, "Production and neurotropism of lentivirus vectors pseudotyped with lyssavirus envelope glycoproteins", MOL THER. Aug. 2001, 4(2), pp. 149-156.
Mazarakis et al, "Rabies virus glycoprotein pseudotyping of lentiviral vectors enables retrograde axonal transport and access to the nervous system after peripheral delivery", Human Molecular Genetics, vol. 10, No. 19, Sep. 15, 2001, pp. 2109-2121.
Azzouz et al, Gene transfer to the nervous system using Equine Infectious Anaemia Virus based lentiviral vectors, Society for Neuroscience Abstracts, & 31$^{st}$ Annual Meeting of the Society for Neuroscience, San Diego, California, Nov. 10-15, 2001.
Azzouz, M., Ralph, S., Wong, L.F., Day, D., Askham, Z., Barber, R.D., Mitrophanous, K.A., Kingsman, S.M., and Mazarakis, N.D. (2004). Neuroprotection in a rat Parkinson model by GDNF gene therapy using EIAV vector. Neuroreport 15, 985-990.
Bensadoun, J.C., Deglon, N., Tseng, J.L., Ridet, J.L., Zurn, A.D., and Aebischer, P. (2000). Lentiviral vectors as a gene delivery system in the mouse midbrain: cellular and behavioral improvements in a 6-OHDA model of Parkinson's disease using GDNF. Experimental neurology 164, 15-24.
Bilang-Bleuel, A., Revah, F., Colin, P., Locquet, I., Robert, J.J., Mallet, J., and Horellou, P. (1997). Intrastriatal injection of an adenoviral vector expressing glial-cell-line-derived neurotrophic factor prevents dopaminergic neuron degeneration and behavioral impairment in a rat model of Parkinson disease. Proceedings of the National Academy of Sciences of the United States of America 94, 8818-8823.

(Continued)

Primary Examiner—Robert M Kelly
(74) Attorney, Agent, or Firm—Nixon & Vanderhye P.C.

(57) ABSTRACT

The invention relates to a defective lentivirus which is pseudotyped with a lyssavirus envelope of the PV (rabies virus) or MOK type (Mokola virus), for example, and to the use thereof, especially in the preparation of a composition for in vivo transfer of genes in astrocytes and also for the treatment of disorders of the central nervous system.

5 Claims, 6 Drawing Sheets

OTHER PUBLICATIONS

Brizard, M., Carcenac, C., Bemelmans, A.P., Feuerstein, C., Mallet, J., and Savasta, M. (2006). Functional reinnervation from remaining DA terminals induced by GDNF lentivirus in a rat model of early Parkinson's disease. Neurobiology of disease 21, 90-101.

Choi-Lundberg, D.L., Lin, Q., Chang, Y.N., Chiang, Y.L., Hay, C.M., Mohajeri, H., Davidson, B.L., and Bohn, M.C. (1997). Dopaminergic neurons protected from degeneration by GDNF gene therapy. Science (New York, NY 275, 838-841.

Gash, D.M., Zhang, Z., Ovadia, A., Cass, W.A., Yi, A., Simmerman, L., Russell, D., Martin, D., Lapchak, P.A., Collins, F., et al. (1996). Functional recovery in parkinsonian monkeys treated with GDNF. Nature 380, 252-255.

Georgievska, B., Kirik, D., and Bjorklund, A. (2002a). Aberrant sprouting and downregulation of tyrosine hydroxylase in lesioned nigrostriatal dopamine neurons induced by long-lasting overexpression of glial cell line derived neurotrophic factor in the striatum by lentiviral gene transfer. Experimental neurology 177, 461-474.

Georgievska, B., Kirik, D., Rosenblad, C., Lundberg, C., and Bjorklund, A. (2002b). Neuroprotection in the rat Parkinson model by intrastriatal GDNF gene transfer using a lentiviral vector. Neuroreport 13, 75-82.

Grondin, R., et al (2002). Chronic, controlled GDNF infusion promotes structural and functional recovery in advanced parkinsonian monkeys. Brain 125, 2191-2201.

Iravani, M.M., et al (2001). GDNF reverses priming for dyskinesia in MPTP-treated, L-DOPA-primed common marmosets. The European journal of neuroscience 13, 597-608.

Kirik, D., et al (2000a). Preservation of a functional nigrostriatal dopamine pathway by GDNF in the intrastriatal 6-OHDA lesion model depends on the site of administration of the trophic factor. The European journal of neuroscience 12, 3871-3882.

Kirik, D., et al (2000b). Long-term rAAV-mediated gene transfer of GDNF in the rat Parkinson's model: intrastriatal but not intranigral transduction promotes functional regeneration in the lesioned nigrostriatal system. J Neurosci 20, 4686-4700.

Kordower, J.H., et al (2000). Neurodegeneration prevented by lentiviral vector delivery of GDNF in primate models of Parkinson's disease. Science (New York, NY 290, 767-773).

Lin, L.F., et al (1993). GDNF: a glial cell line-derived neurotrophic factor for midbrain dopaminergic neurons. Science (New York, NY 260, 1130-1132.

Mandel, R.J., et al (1997). Midbrain injection of recombinant adeno-associated virus encoding rat glial cell line-derived neurotrophic factor protects nigral neurons in a progressive 6-hydroxydopamine-induced degeneration model of Parkinson's disease in rats. Proceedings of the National Academy of Sciences of the United States of America 94, 14083-14088.

McCown, T.J., et al (1996). Differential and persistent expression patterns of CNS gene transfer by an adeno-associated virus (AAV) vector. Brain research 713, 99-107.

Naldini, L., et al (1996). Efficient transfer, integration, and sustained long-term expression of the transgene in adult rat brains injected with a lentiviral vector. Proceedings of the National Academy of Sciences of the United States of America 93, 11382-11388.

Rosenblad, C., et al (1999). Protection and regeneration of nigral dopaminergic neurons by neurturin or GDNF in a partial lesion model of Parkinson's disease after administration into the striatum or the lateral ventricle. The European journal of neuroscience 11, 1554-1566.

Rosenblad, C., et al (1998). Intrastriatal glial cell line-derived neurotrophic factor promotes sprouting of spared nigrostriatal dopaminergic afferents and induces recovery of function in a rat model of Parkinson's disease. Neuroscience 82, 129-137.

Zennou, V., et al (2001). The HIV-1 DNA flap stimulates HIV vector-mediated cell transduction in the brain. Nature biotechnology 19, 446-450.

Braekelandt et al "Characterization of Lentiviral Vector-Mediated Gene Transfer in Adult Mouse Brain" Human Gene Therapy 13:841-853 (2002).

Bjorklund et al "Towards a neuroprotective gene therapy for Parkinson's disease use of adenovirus, AAV and lentivirus vectors for gene transfer of GDNF to the nigrostriatal system in the rat Parkinson model" Brain Research (2000) 82-89.

Blomer, U., L. et al 1997 Highly efficient and sustained gene transfer in adult neurons with a lentivirus vector. J Virol 71:6641-9.

Ceravolo, R., P. et al 2006. Assessing neuroprotection in Parkinson's disease: from the animal models to molecular neuroimaging in vivo. J Neural Transm Suppl:133-41.

Georgievska, B., D. et al 2002. Aberrant sprouting and downregulation of tyrosine hydroxylase in lesioned nigrostriatal dopamine neurons induced by long-lasting overexpression of glial cell line derived neurotrophic factor in the striatum by lentiviral gene transfer. Exp Neurol 177:461-74.

Georgievska, B., D. et al 2002. Neuroprotection in the rat Parkinson model by intrastriatal GDNF gene transfer using a lentiviral vector. Neuroreport 13:75-82.

Kafri, T., U. et al. 1997. Sustained expression of genes delivered directly into liver and muscle by lentiviral vectors. Nat Genet 17:314-7.

Killebrew, D., et al. 2004. Pathogenesis of HIV-associated non-Hodgkin lymphoma. Curr HIV Res 2:215-21.

Kink, D., C. et al 2000. Preservation of a functional nigrostriatal dopamine pathway by GDNF in the intrastriatal 6-OHDA lesion model depends on the site of administration of the trophic factor. Eur J Neurosci 12:3871-82.

Kink, D., C. et al 2000. Long-term rAAV mediated gene transfer of GDNF in the rat Parkinson's model: intrastriatal but not intranigral transduction promotes functional regeneration in the lesioned nigrostriatal system. J Neurosci 20:4686-700.

Philippe, S., C. et al 2006. Lentiviral vectors with a defective integrase allow efficient and sustained transgene expression in vitro and in vivo. Proc Natl Acad Sci U S A 103:17684-9.

Ridet, J. L., C. et al 2003. Transplantation of human adult astrocytes: efficiency and safety requirements for an autologous gene therapy. J Neurosci Res 72:704-8.

Senguena, C., et al 2001. Primary adult human astrocytes as an ex vivo vehicle for beta-glucuronidase delivery in the brain. Mol Ther 3:875-8 1.

Simoha, N., et al 2007. The 6-hydroxydopamine model of Parkinson's disease. Neurotox Res 11:151-67.

Themis, M., et al 2005. Oncogenesis following delivery of a nonprimate lentiviral gene therapy vector to fetal and neonatal mice. Mol Ther 12:763-71.

Woods, N. B., et al 2006. Gene therapy: therapeutic gene causing lymphoma. Nature 440:1123.

Declaration of Chamsy Sarkis executed Sep. 19, 2006.

Declaration of Chamsy Sarkis executed May 23, 2007.

Declaration of Chamsy Sarkis executed Mar. 10, 2008.

Declaration of Chamsy Sarkis executed Feb. 23, 2010.

Kahle (2001) Emerging Therapeutic Targets 5(1):125-132 (cited by Examiner on p. 5 of Office Action dated Nov. 24, 2009); Pfeifer (2002) Annu. Rev. Genomics. Human Genet 2:177-211 (cited by Examiner on p. 4 of Office Action dated Jun. 13, 2008 and p. 5 of the Office Action dated Nov. 15, 2007).

Johnson-Saliba (2001) Curr. Drug Targets 2:371-99 (cited by Examiner on p. 4 of Office Action dated Jun. 13, 2008 and p. 5 of the Office Action dated Nov. 15, 2007).

Shoji (2004) Current Pharmaceutical Design 10:785-796 (cited by Examiner on p. 5 of Office Action dated Jun. 13, 2008 and p. 6 of the Office Action dated Nov. 15, 2007).

Jacobsen (2002) Curr. To. Med. Chem 2(4):343-52 "Alzheimer's Disease: An Overview of Current and Emerging Therapeutic Strategies" (cited by Examiner on p. 5 of the Office Action date Mar. 23, 2006).

Rainov (2001) Current Gene Therapy 1:367-383 "Vector Delivery Methods and Targeting Strategies for Gene Therapy of Brain Tumors" (contained in PTO IFW).

Dietzchold et al. 1996. Rhabdoviruses, p. 1137-1159. In Fields Virology B. Fields, D. Knipe and P. Howley (ed.), Third ed, vol. 1. Lippincott—Raven, Philadelphia.

Callaway "Transneuronal circuit tracing with neurotropic viruses." Current Opinion in Neurobiology 2008, 18:617-623; Pertusa et al "Expression of GDNF transgene in Astrocytes Improves Cognitive Deficits in Aged Rats" Neurobiology of Aging 29 (2008) 1366-1379.

Alonso et al "Turning Astrocytes from the Rostral Migratory Stream into Neurons: A Role for the Olfactory Sensory Organ" The Journal of Neuroscience, Oct. 22, 2008, 28(43): 11089-11102.

* cited by examiner

| | Vector | Simple inj. | Double inj. | Triple Inj. |
|---|---|---|---|---|
| Repeat injection of the same vector | MOK | + | ++ | + |
| | VS | ± | + | + |
| | PV | ± | + | + |
| Double injection PBS + vector | PBS/MOK | ± | MOK/PBS | + |
| | PBS/VS | + | VSV/PB | - |
| | PBS/PV | ± | PV/PB | - |
| Double injection different vectors | MOK/VSV | + | MOK/PV | + |
| | VSV/MOK | + | VSV/P | +++ |
| | PV/MOK | + | PV/VS | ± |

METHODS OF GENE TRANSFER TO ASTROCYTES WITH MOKOLA VIRUS PSEUDOTYPED LENTIVIRUS VECTORS

This application is the US national phase of international application PCT/FR02/01833 filed 31 May 2002 which designated the U.S. and claims benefit of FR 01/07239, dated 1 Jun. 2001, the entire contents of each of which is hereby incorporated by reference.

The present invention relates to gene transfer into the nervous system by means of pseudotyped viruses. It relates in particular to the use of an envelope (glycoprotein) of an enveloped virus, for example lyssavirus, for pseudotyping a defective lentiviral vector and to the targeting of a cell population or subpopulation of the nervous system. The present invention also relates to methods and compositions intended for the selective transfer of target genes into particular nerve cell populations, in particular into astrocytes, in vitro, ex vivo and in vivo, and also for the treatment of disorders of the central nervous system and/or of the ocular system.

Gene transfer into the nervous system has many applications, in experimental, therapeutic, research fields, etc. Thus, this transfer may make it possible to carry out labeling, toxicity and quality studies, to construct pathological models, to restore deficiencies, to express therapeutic products (for example proteins, RNAs, etc.), etc.

Various approaches have been envisioned in the prior art for this transfer, such as the use of viral vectors (retroviruses, AAVs, adenoviruses, etc.), the injection of plasmids, the transplanting of cells, the implantation of encapsulated cells, etc. Each of these approaches has advantages and disadvantages, in terms of efficiency, security, industrial use, selectivity, stability, etc.

Thus, the use of viral vectors is advantageous in terms of transfer efficiency, associated with the natural properties of infection of viruses. Among the viruses used, the applicant has been interested more particularly in retroviruses.

In the first steps of infection, retroviruses deliver their nucleoprotein core into the cytoplasm of the target cell. Reverse transcription of the viral genome then takes place, while the core transforms into a preintegration complex. The complex must reach the nucleus in order to enable integration of the viral DNA into the chromosomes of the host cell.

Many oncoretrovirus-derived retroviral vectors allow the integration of a transgene into the genome of target cells, but these vectors are only capable of transducing dividing cells. This restriction limits their use to gene transfer ex vivo or to organs in which the cells are mitotically active.

A means of bypassing this obstacle consists in using lentivirus-derived vectors. Lentiviruses are complex retroviruses capable of integrating into the genome of cells which are not mitotically active. These viruses include in particular HIV-1, HIV-2, SIV, FIV, BIV, VISNA, CAEV and EIAV. However, drawbacks associated with the use of lentiviruses lie in particular in the lack of specificity, the potential risks and the difficulties in production. The drawbacks have up until now limited the use of this type of vector for gene transfer in vivo.

The present invention brings a solution to the problems of the prior art and provides novel tools and vectors for gene transfer into the nervous system. The invention lies in particular in the use of viral envelopes for the selective transfer of genes into the nervous system, in particular into certain cell subpopulations of the central nervous system.

The present invention describes, surprisingly, a pseudotyped defective lentiviral vector and its use for the selective transfer of the genes into certain nerve cell populations, and in particular into astrocytes, in vitro, ex vivo and in vivo. Such a targeted gene transfer makes it possible to locally treat a disease affecting the nervous system.

The invention also lies in the use of lyssavirus envelopes for targeting lentiviral vectors to particular nerve cell populations. Lyssaviruses belong to the rhabdovirus family.

The present invention also comprises the preparation of a composition intended for the transfer of genes into astrocytes in vivo, and also the use of this composition in the treatment of disorders of the central nervous system.

DETAILED DESCRIPTION OF THE INVENTION

The present invention describes the pseudotyping of recombinant lentiviral vectors allowing cellular targeting in the nervous system, and more particularly in glial cells of the astrocyte type. These pseudotyped viral vectors are useful for the transfer and the expression in vivo of nucleic acid sequences within astrocytes.

General Structure of the Vectors

Like other retroviruses, lentiviruses have gag, pol and env genes flanked by two LTR (Long Terminal Repeat) sequences. Each of these genes encodes many proteins which are initially expressed in the form of a single precursor polypeptide. The gag gene encodes the internal structural proteins (capsids and nucleocapsids). The pol gene encodes the reverse transcriptase, the integrase and the protease. The env gene encodes the viral envelope glycoprotein and also contains a cis-acting RRE (Rev Responsive Element) responsible for exporting the viral RNA out of the nucleus. The 5' and 3' LTR sequences serve to promote the transcription and the polyadenylation of the viral RNAs. The LTR contains all the other cis-acting sequences necessary for viral replication. Sequences necessary for the reverse transcription of the genome (tRNA primer binding site) and for encapsidation of the viral RNA into particles (site $\Psi$) are adjacent to the 5' LTR. If the sequences necessary for encapsidation (or for packaging of the retroviral RNA into infectious virions) are absent from the viral genome, the genomic RNA will not be actively encapsidated.

The construction of lentiviral vectors for gene transfer applications has been described, for example, in patents U.S. Pat. No. 5,665,577, EP 386 882, U.S. Pat. Nos. 5,981,276 and 6,013,516 or else in patent application WO 99/58701. These vectors comprise a defective lentiviral genome, i.e. a genome in which at least one of the gag, pol and env genes has been inactivated or deleted. These vectors are encapsidated in a protein particle composed of the structural lentiviral proteins and in particular of the envelope glycoprotein.

The recombinant lentiviruses according to the invention are thus genetically modified in such a way that certain genes constituting the native infectious virus are eliminated and replaced with a nucleic acid sequence of interest to be introduced into the target cells. After fusion of the virus with the cell membrane, said virus injects its nucleic acid into the cell and, after reverse transcription, said nucleic acid can integrate into the genome of the host cell. The genetic material thus transferred is then transcribed and possibly translated into proteins inside the host cell.

The lentiviruses of the invention can be prepared from various serotypes, in particular HIV-1, HIV-2, SIV, FIV, BIV, VISNA, CAEV and EIAV. Particularly preferred serotypes are HIV, FIV and EIAV.

Pseudotyping

As indicated above, the invention lies in the demonstration of the targeting properties of lentiviruses pseudotyped with particular envelopes.

The term "pseudotyping" denotes a recombinant virus comprising an envelope different from the wild-type envelope, and thus possessing a modified tropism. In the case of the pseudotyped lentiviruses, they are lentiviruses which have a heterologous envelope of non-lentiviral origin, for example originating from another virus, or of cellular origin.

Pseudotyped HIV-1 vectors described in the prior art comprise the envelope glycoprotein of the vesicular stomatitis virus (VSV). This envelope exhibits advantageous characteristics, such as resistance to ultracentrifugation and a very broad tropism. Unlike other envelopes, such as those of the conventional retroviruses (amphotropic and ecotropic MLV retroviruses or HIV gp120, but also many others), the VSV glycoprotein is not labile after ultracentrifugation. This makes it possible to concentrate the viral supernatents and to obtain high infectious titers. Moreover, this envelope confers on the virions a very broad tropism, in particular in vitro, allowing the infection of a very large number of cell types. The receptor for this envelope is thought to be a phosphatidylserine motif present at the surface of many cells of various species.

A particular characteristic of the invention consists in using an envelope (glycoprotein) of a lyssavirus, and in particular of a virus of the rabies virus serogroup: Rabies (RAB) (Tuffereau C., Benejean J., Blondel D., Kieffer B., Flamand A.; Low-affinity nerve-growth factor receptor (P75NTR) can serve as a receptor for rabies virus; EMBO J., 1998 December 15;17 (24): 7250-9); Duvenhague (DUV), European bat type 1 (EB-1), European bat type 2 (EB-2), Lagos bat (LB), Mokola (MOK) (Bourhy H, Kissi B, Tordo N. Molecular diversity of the Lyssavirus genus. Virology. 1993 May;194 (1):70-81.) (Badrane H, Bahloul C, Perrin P, Tordo N. Evidence of two Lyssavirus phylogroups with distinct pathogenicity and immunogenicity. J Virol. 2001 April;75(7):3268-76), Kotonkan (KOT), Obodhiang (OBD) and Rochambeau (RBU) (Della-Porta AJ, Brown F. The physicochemical characterization of bovine ephemeral fever virus as a member of the family Rhabdoviridae. J Gen Virol. 1979 July;44(1):99-112.) or any chimeric composition of these envelopes.

Unlike VSV, the present application shows that the rabies and Mokola viruses have a tropism in animals which is very specific for the nervous system. The system of entry of these viruses also depends on specific receptors. For rabies, several candidates have been proposed as receptors: acetylcholine receptors (nicotinic receptors in particular), NCAM molecules (140 and 180 kDa) and also low-affinity NGF receptors (p75).

In a preferred embodiment, the invention uses lentiviral vectors, for example of the HIV type, pseudotyped with an envelope of the PV (rabies virus) or MOK (Mokola virus) type.

The invention in fact shows, surprisingly, that this type of envelope allows cellular targeting, in particular the targeting of glial cells of the astrocyte type.

The MOK and PV pseudotypes can also be ultracentrifuged just like VSV, and therefore make it possible to concentrate supernatants. They also make it possible, surprisingly, to obtain a tropism which is restricted relative to VSV, and therefore a cellular targeting in vivo in the CNS. It is also possible to obtain stable clones without an induction system for the PV and MOK glycoproteins. These stable clones can be used to develop stable encapsidation lines for the production of lentiviral vectors pseudotyped with one of these two envelopes.

The invention therefore relates to lyssavirus (in particular PV and/or MOK) envelopes which make it possible to pseudotype lentiviral vectors for specifically transducing astrocytes.

It also relates to the use of these pseudotyped lentiviral vectors, for preparing a composition intended for gene transfer into astrocytes in vivo. According to a particularly advantageous characteristic of the invention, the defective lentivirus used is the human immunodeficiency virus. According to another particularly advantageous characteristic, the lentivirus used comprises one or more viral proteins selected from TAT and REV.

Production of Recombinant Pseudotyped Lentiviral Vectors

The lentiviral vectors according to the invention can be prepared in various ways, by transient transfection(s) into stable lines and/or by means of helper viruses.

The method according to the invention provides, according to a particularly preferred embodiment, for the combination of a minimum of three vectors in order to produce a recombinant virion or a recombinant retrovirus.

A first vector provides the lentiviral vector comprising the cis-acting viral sequences necessary for the correct functioning of the viral cycle. Such sequences include one or more lentiviral LTRs, a Psi packaging sequence of lentiviral origin, reverse transcription signals, a promoter and/or an enhancer and/or polyadenylation sequences. The first vector also contains a cloning site for a heterologous nucleic acid sequence to be transferred into a nonproliferative cell. In this vector, the LTRs can also be modified so as to improve the expression of the transgene or the safety of the vector. Thus, it is possible to modify, for example, the sequence of the 3' LTR by eliminating the U3 region (WO 99/31251). According to a preferred embodiment of the invention, it is a vector plasmid comprising a recombinant lentiviral genome of sequence LTR-psi-RRE-flap-Promoter-transgene-LTR which allows expression of the vector RNA which will be encapsidated in the virions. The transgene may encode, for example, the following trophic factors: CNTF, NGF, NT3, NT4, FGF, PDGF, etc., or enzymes which restore a deficient metabolic activity, for example: TH, AADC, GTPC, β-glucuronidase, etc. The transgene is typically placed under the control of a transcriptional promoter, which may be homologous with respect to the transgene or heterologous, for example a viral, cellular, synthetic, etc. promoter. The promoter used may be constitutive or regulated, weak or strong, tissue-specific or ubiquitous, etc. Use is typically made of a viral promoter such as CMV, LTR, TK, etc, or a cellular promoter such as PGK, Rho, etc. Tissue-specific promoters can be used, even though the vectors of the invention already confer an expression selectivity characteristic.

A second vector, for trans-complementation, provides a nucleic acid encoding a gag lentiviral protein and a pol lentiviral protein. These two proteins are derived from a lentivirus and preferably originate from HIV. The second vector is devoid of encapsidation sequence, of sequence encoding an envelope and, advantageously, is also devoid of lentiviral LTRs. As a result, the sequences encoding gag and pol proteins are advantageously placed under control of a heterologous promoter, for example a viral, cellular, etc. promoter, which may be constitutive or regulated, weak or strong. It is preferably a trans-complementing plasmid comprising a sequence CMV-Δpsi-gag-pol-Δenv-PolyA. This plasmid allows the expression of all the proteins necessary for the formation of empty virions, except the envelope glycoproteins. It is understood that the gag and pol genes may also be carried by different plasmids.

A third vector provides a nucleic acid which allows the production of the chosen envelope (env) glycoprotein.

This envelope may be chosen from the envelopes mentioned above, in particular an envelope of a rhabdovirus, more particularly of a lyssavirus, even more preferably MOK or PV. This vector is devoid of encapsidation sequence and of sequences encoding gag or pol and, advantageously, is also devoid of lentiviral LTRs.

Advantageously, the three vectors used do not contain any homologous sequence sufficient to allow a recombination. The nucleic acids encoding gag, pot and env may advantageously be cDNAs prepared according to conventional techniques, from sequences of the viral genes available in the prior art and on databases, as illustrated in the examples.

For the production of the replication-defective recombinant viruses, the vectors described above are introduced into competent cells and the viruses produced are harvested. The cells used may be any competent cell, preferably mammalian cell, for example animal or human cell, which is non pathogenic. Mention may, for example, be made of 293 cells, embryonic cells, fibroblasts, muscle cells, etc.

The invention therefore lies in a method for preparing a pseudotyped defective recombinant lentivirus, comprising transfection of a population of competent cells with a combination of vectors as described above, and recovery of the viruses produced.

The invention thus relates to a particularly advantageous method for producing lentiviruses capable of targeting the in vivo expression of a transgene, in human astrocytes, comprising transfection of competent cells with:
 a) a vector plasmid comprising a sequence LTR-psi-RRE-flap-Promoter-transgene-LTR(ΔU3),
 b) a trans-complementing plasmid comprising a sequence CMV-Δpsi-gag-pol-Δenv-PolyA,
 c) an envelope plasmid comprising a sequence CMV-env-PolyA, the envelope being an envelope of the Mokola virus or of the rabies virus.

The lentiviruses of the invention may also be prepared from an encapsidation cell line producing one or more gag, pol and env proteins. According to a particular embodiment, use is made of a cell line expressing the env protein in a stable manner (i.e. from a sequence integrated into its genome). Indeed, unlike the lentiviral envelopes, the MOK or PV envelopes, for example, do not exhibit any significant toxicity for the cells and can be expressed stably and constitutively (or in a regulated manner) in a line.

As a result, in a particular embodiment, the method of the invention comprises transfecting only two vectors (the lentiviral vector and the trans-complementing vector) into a cell line expressing the chosen env protein. The cells used to prepare such a line are, for example, the competent cells mentioned above. Such a line also constitutes a subject of the present application.

According to another embodiment, the line used also expresses the lentiviral gag and pol proteins. In this case, the method simply comprises transfection of the lentiviral vector.

In this regard, it is possible to use a lentiviral encapsidation cell such as that described in patent application WO 99/58701, in which the gag and pol genes of HIV are present on separate constructs.

Preferably, the lentiviruses produced are derived from the HIV-1, HIV-2, SIV, FIV, BIV, VISNA, CAEV or EIAV virus.

Surprisingly, the present application shows that the pseudotyped lentiviral vectors thus obtained are capable of preferentially infecting certain nerve cell subpopulations, in particular astrocytes, in vivo. The term "preferentially" should be understood to mean that the lentiviruses according to the invention target essentially astrocytes but are, nevertheless, capable of transfecting other cell types, such as other glial cells or neurons. Other nerve cell subpopulations which may be targeted by vectors of the invention are, for example, microglial cells, endothelial cells or oligodendrocytes. In a particular application concerning gene transfer into the eye, the vectors of the invention pseudotyped with the Mokola envelope allow selective transfer to the cells of the pigment epithelium.

The lentiviruses according to the invention may, finally, be used for producing a pharmaceutical composition intended to treat a disease of the nervous system or a neurodegenerative disease, and in particular Alzheimer's disease, Parkinson's disease, Huntington's Chorea, SLA or SMA, ocular degenerations or else traumas of the central nervous system (cerebral attack, epilepsy, spinal cord lesions, etc.), diseases affecting the central nervous system (MPS, etc.), glioblastomas or astrocytomas, or metabolic diseases affecting the nervous system (mucopolysaccharidosis, Charcot-Marie-Tooth disease, etc.).

Another subject of the invention lies in the combined use of several lentiviruses pseudotyped with a different lyssavirus envelope, for the purpose of transferring and expressing a nucleic acid wherein the cells of the nervous system. The combined use may comprise sequential administrations of the various viruses, or a simultaneous administration.

As indicated above, the invention may allow the transport and the expression of multiple nucleic acids wherein nerve cells, such as, for example, catalytic nucleic acids (antisense nucleic acids, ribozymes, etc.), nucleic acids encoding growth factors, trophic factors, cytokines, colony stimulating factors, anticancer agents, toxins, enzymes, neurotransmitters or their precursors, etc.

The pharmaceutical composition containing the lentivirus according to the invention may be administered to a patient intracerebrally or systemically given the particular tropism of the pseudotyped lentiviral vectors, in particular for astrocytes. Thus, it may be an administration given intracerebrally, intra-striatally, intra-venously, intra-arterially, into the sub-retinal space, etc. Preferred modes of injection are intracerebral injection and injection into the subretinal space. For the use for gene transfer into the eye, viruses pseudotyped with a Mokola envelope are most particularly preferred.

The composition is advantageously administered at a rate of $10^2$ to $10^9$ particles per dose, typically of $10^3$ to $10^8$. The lentiviruses may be conditioned in any suitable solution, such as a saline, isotonic, buffered solution, optionally combined with stabilizing agents such as isogenic albumin or any other stabilizing protein, glycerol, etc., and also adjuvants such as polybrene or DEAE dextrans, etc.

Other advantages of the invention are illustrated in greater detail in the following examples, which should be considered as nonlimiting illustrations.

EXAMPLES

1. Production of the Pseudotyped Viruses (VSV, MOK and PV)

The vectors of sequence LTR-Ψ-RRE-flap-CMV-GFP-LTR or LTR-Ψ-RRE-flap-PGK-GFP-LTR(AU3), the trans-complementing plasmid Δ8.71 and the envelope plasmids CMV-VSV-G, CMV-MOK-G or CMV-Rab-G were used to produce the pseudotyped viruses.

On day 0, 160 cm$^2$ dishes filled with 293T cells at low confluency (approximately 50%) are prepared.

On day 1, the culture medium is replaced with fresh medium and the transfection is performed with the three plasmids.

On day 2, the medium is again changed.

On day 3, the supernatent is harvested and then treated with DNAse for 15 minutes at 37° C. It is then centrifuged at 3000 rpm for 5 minutes in order to remove the cellular debris, and ultracentrifuged at 4° C. for 1 h 30 mins (SW28 rotor) and then resuspended in 1×PBS. The residues are then removed by short centrifugations at 8000 rpm for 30 seconds. The supernatant thus purified is then aliquoted and stored at −80° C.

The stocks are titrated by ELISA assay of the capsid protein (p24). The titer is expressed in nanograms of p24 molecules per microliter of supernatent.
Stocks #1: CMV-GFP
VSV: 78 ng p24/μl
MOK: 19 ng p24/μl
PV: 29 ng p24/μl
Stocks #2: CMV-GFP
VSV: 89 ng p24/μl
MOK: 30 ng p24/μl
PV: 64 ng p24/μl
Stocks #3: PGK-GFP
VSV: 30 ng p24/μl
MOK: 56 ng p24/μl
PV: 21 ng p24/μl 2. Transduction of Cell Lines in vitro with the Pseudotyped Viruses Nerve cell transduction was tested on 7 different lines with the vectors containing a CMV-GFP cassette. The lines tested are as follows:
CHP212 and SKNSH: human neuroblastomas
PC12 : rat pheochromocytoma
Cath.a and Cath.B: mouse cathecolaminergic central lines transformed with SV40
Path.1 and Path.2: mouse catecholaminergic peripheral lines transformed with SV40

A total of 100 000 cells are placed in the wells of a 24-well plate. The following day, the cells are transfected with cultured medium containing 20 ng of the vector p24 in a final volume of 200 μl. The cells are incubated with the virus overnight. The following day, the medium is changed and replaced with a fresh medium without virus. The cells are dissociated and fixed for flow cytometry (FACS) analysis, 48 hours after the withdrawal of the viruses.

The SKNSH, CHP212 and PC12 cells were transfected with stocks#1. The Cath and Path cells were transfected with stocks#2.

FIGS. 1A, 1B, 1C and 2A, 2B, 2C demonstrate very efficient transduction, with the VSV pseudotypes, of all the lines tested (by percentage). The variations in intensity reflect the relative activity of the CMV promoter in the various lines tested (GFP X-mean).

On the other hand, the PV pseudotypes efficiently transduce (greater than 10%) only the human lines CHP212 and SKNSH.

The MOK pseudotypes efficiently transduce the CHP212, SKSNH, Cath.b, Path.1 and Path.2 lines.

Thus, it is clearly apparent that the MOK and PV pseudotypes exhibit a host restriction which does not exist in VSV, in the lines tested.

3. In vivo Transduction of C57B16 Mouse Brain

For each pseudotype, three C57B16 mice (8 weeks old) were given an injection in the striatum. A dose of 20 ng of p24 (CMV-GFP vectors) was injected in a volume of 2 microliters. The stereotaxic coordinates used relative to lambda are: A: +4.6; L: +2.2; V1: −3.5 (1 μl) and V2: −3.3 (1 μl). The injection rate is 0.25 μl/min.

The mice are sacrificed a week after injection. The brains of two mice are perfused (4% PFA) and the third is frozen without perfusion. The brains are sectioned on a cryostat in the zone of injection (20 μm thickness).

The GFP expression can be visualized directly under a fluorescence microscope. The phenotype of the transduced cells is determined by immunolabeling of the sections with an anti-GFAP antibody for the astrocytes, with an anti-NeuN antibody for the neurones and with an anti-CNPase antibody for the oligodendrocytes.

Analysis of the co-expression of the GFP and of the various markers used is carried out on a confocal microscope.

The results obtained show that the VSV pseudotypes transduce various cell populations, including the astrocytes and the neurones.

On the other hand, in the case of the MOK-pseudotype lentiviruses, astrocytes are specifically transduced. There appears to be some very rare transduction of neurones. Similarly, for the PV pseudotypes, only the astrocytes appear to be transduced.

Furthermore, the quantity of cells expressing GFP is very high with the VSV and MOK pseudotypes (comparable levels), even though the number of cells transduced with the PV pseudotypes appears to be lower.

To confirm these results of preferential targeting of astrocytes with the pseudotypes using MOK and PV, injections were performed under similar conditions with the PGK-GFP vectors. In this experiment, a dose of 60 ng of VSV- and MOK-pseudotype p24 was injected into C57B16 mouse brains.

The double labeling experiments with a neurone marker (NeuN) and an astrocyte marker (GFAP) show a solely astrocytic tropism for the MOK pseudotypes, whereas many neurones are transduced with the VSV pseudotypes, thus confirming the specificity of infection of astrocytes with MOK.

Table summarizing the phenotyping results:

|         | NeuN | GFAP | CNPase |
|---------|------|------|--------|
| VSV-CMV | +    | +++  | −      |
| MOK-CMV | −    | ++++ | −      |
| PV-CMV  | −    | +    | −      |
| VSV-PGK | +++  | +    | nd     |
| MOK-PGK | −    | +++  | nd     |
| PV-PGK  | −    | −    | nd     |

4. Study of the Immune Reaction (Multiple Injections)

This experiment was carried out with the aim of studying the possibility of performing repeat injections with the various pseudotypes. Vectors pseudotyped with the same glycoprotein were injected twice or three times into the C57Bl6 mouse brain. The combination of repeat injections with two different pseudotypes was also performed in order to test the immune cross reactions between the various pseudotypes.

The GFP expression is visualized directly by fluorescence. In all cases, it is possible to detect GFP+ cells within the site of the final injection, which is a sign of a weak immune reaction.

A more detailed study of the CTL reaction (T lymphocyte cellular reaction) was carried out by immunolabeling directed against the CD4 and CD8 antigens.

When a single injection is given, the CTL reaction (CD4 and CD8) is very weak, i.e. virtually zero, in the control animals which were given only saline solution.

When two successive injections are given, the reaction observed is very moderate (CD4 and CD8 greater than PBS) but much less than that caused by a simple injection of adenovirus for example.

When three successive injections are given, the CD4 and CD8 reaction is relatively significant. The vectors are not however entirely neutralized since expression is found within the site of the third injection.

The CD4/CD8 (T lymphocyte) reaction may be caused either by the vector (the envelope glycoprotein in particular) or by the expression of the GFP transgene.

These experiments confirm the absence of immune reaction in vivo after several injections, and demonstrate the possibility of giving repeat injections in therapeutic or experimental approaches.

Figure 1:
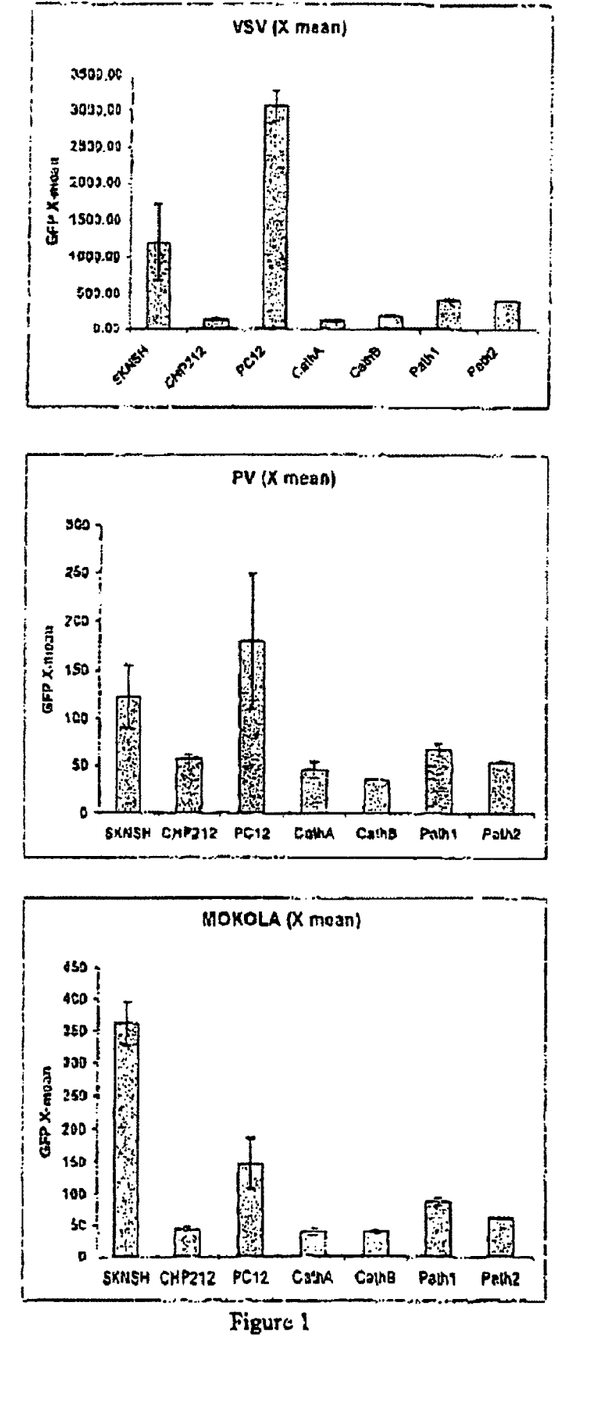
FIG. 1: Mean GFP intensity in the transduced cells.
Figure 2:
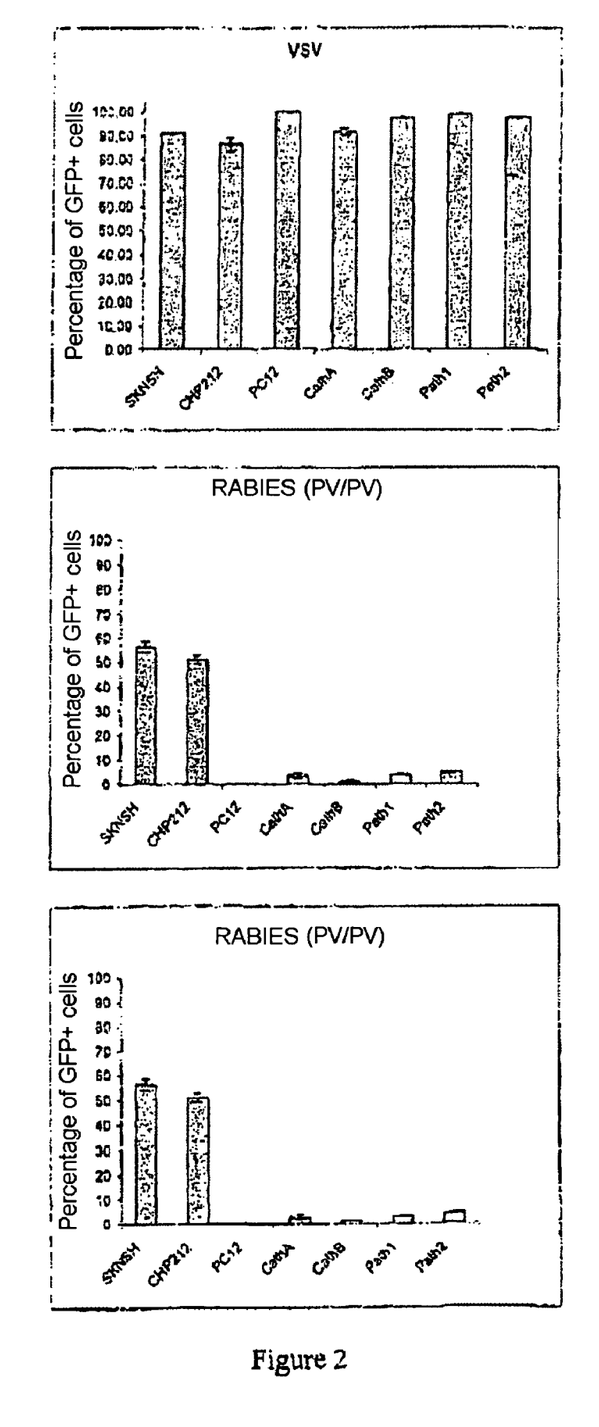
FIG. 2: Percentage of transduced cells.
Figure 3:
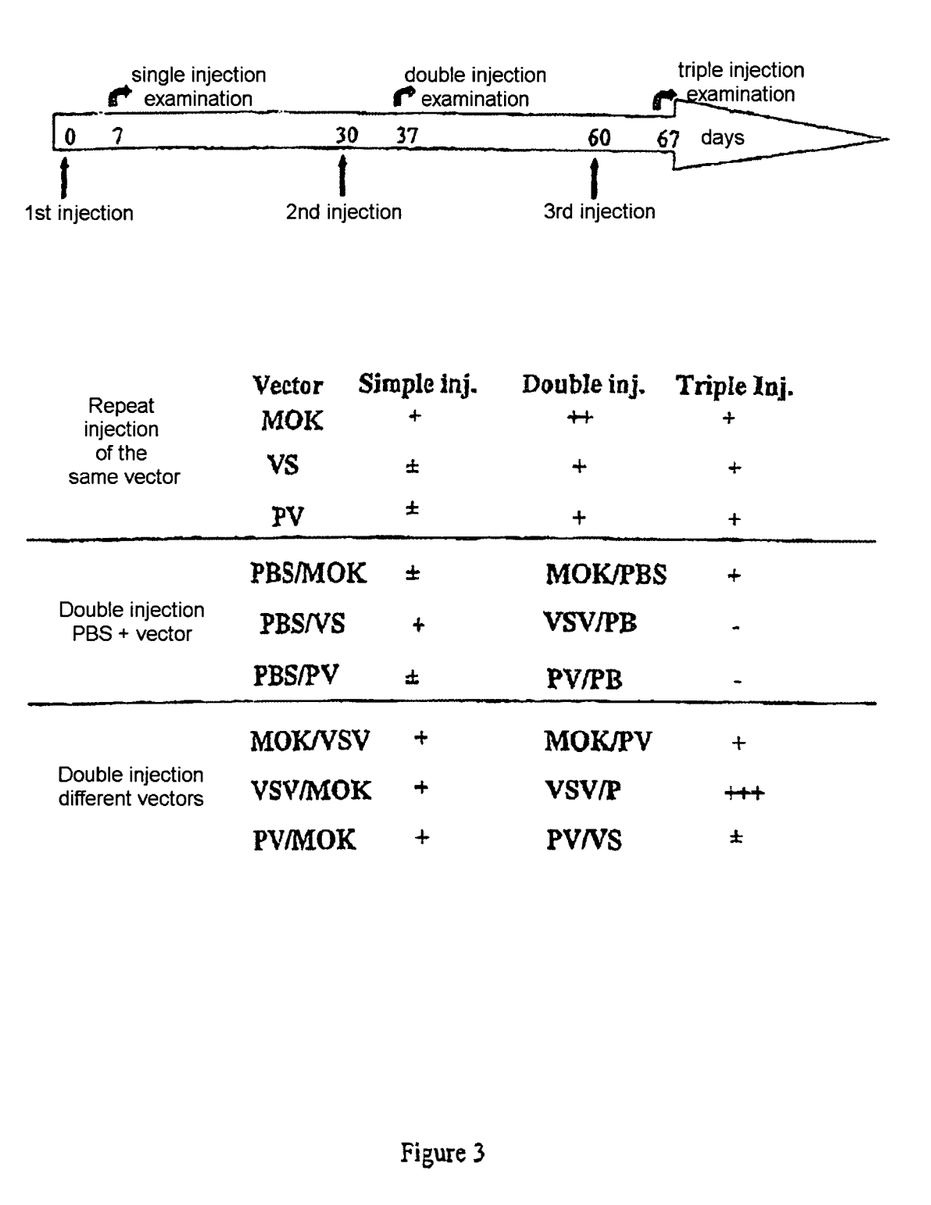
FIG. 3: Progression of the experiment—immune response (CD4/CD8)
Figure 4:
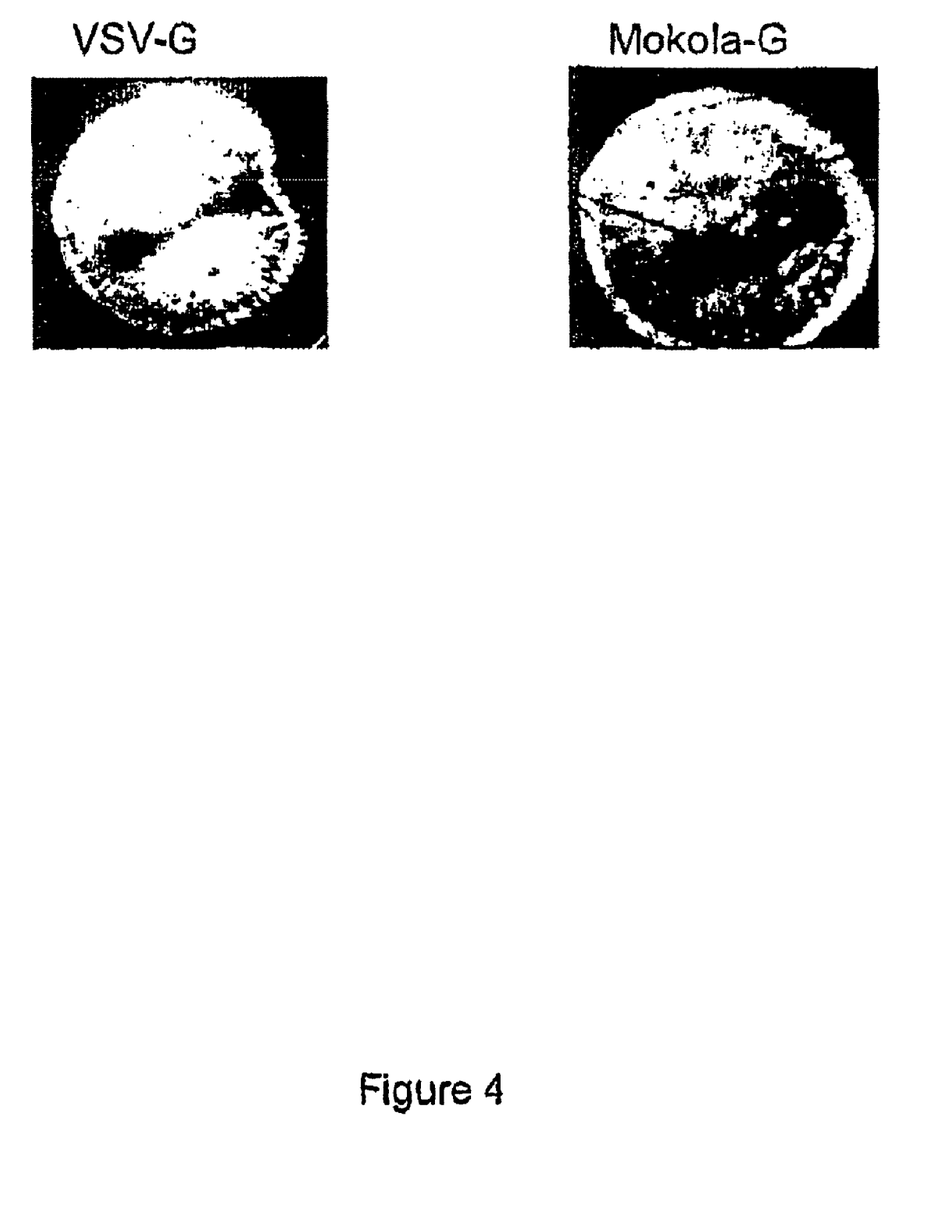
FIG. 4: Angiography of eyeballs injected subretinally with a vector derived from HIV-1 and expressing GFP under the control of the CMV promoter. On the left is the vector pseudotyped with the VSV-G protein and on the right is the vector pseudotyped with the Mokola-G protein.
Figure 5:
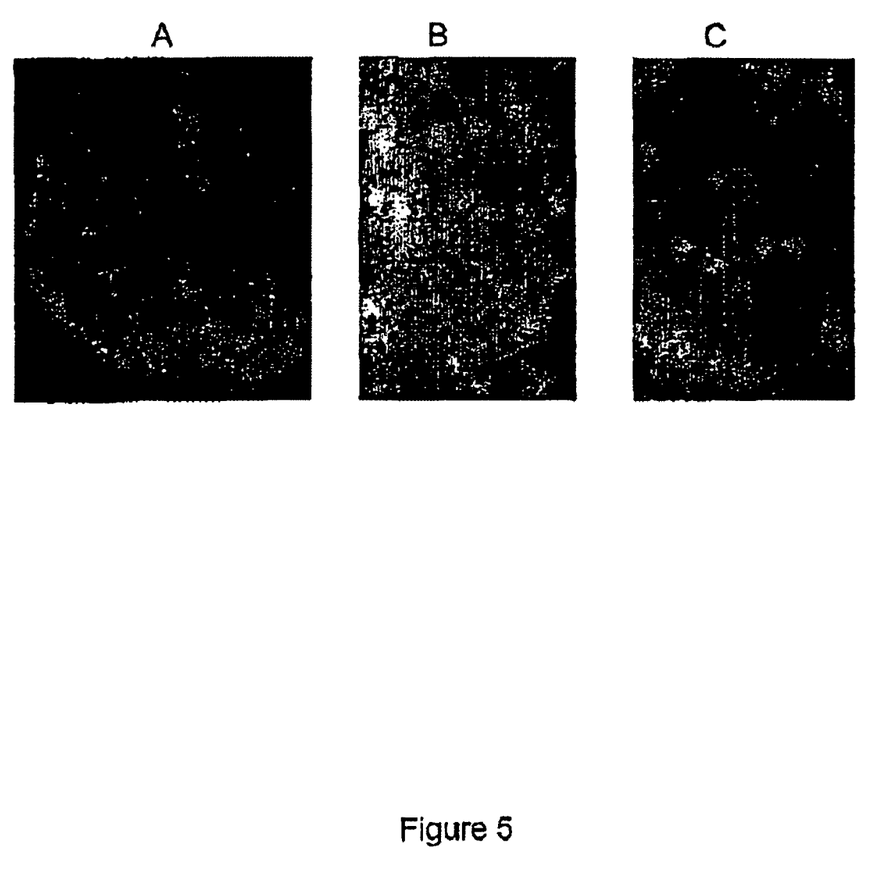
FIG. 5: Pigment epithelium of eyeballs injected subretinally with a vector derived from HIV-1 and expressing GFP under the control of the CMV promoter. (A) view of the entire zone transduced. (B) vector pseudotyped with the VSV-G protein; (C) vector pseudotyped with the Mokola-G protein. In the transduced zone, 100% of the cells express GFP. The hexagonal and binuclear appearance of the cells makes it possible to affirm that it is indeed the pigment epithelium.
Figure 6:
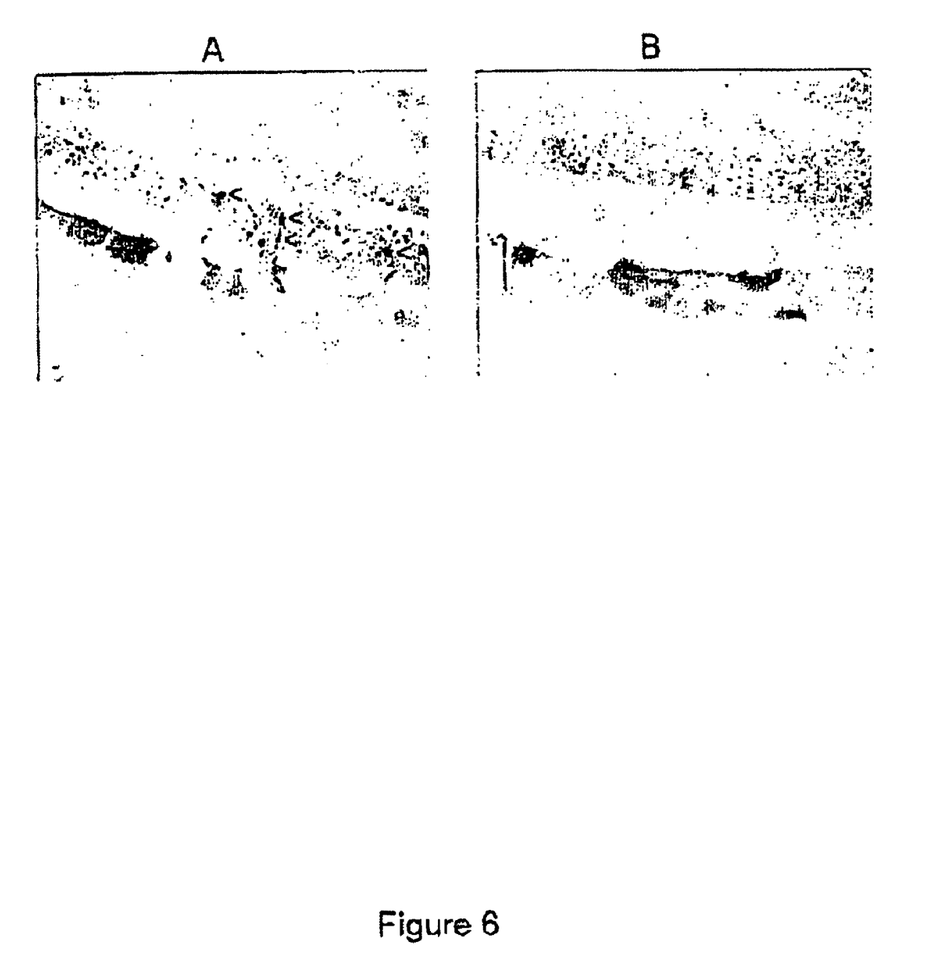
FIG. 6: Anti-GFP immunohistochemistry on thin sections of retina. With the vector pseudotyped with VSV-G (A), labeled cells are detected in the photoreceptor layer (arrows). With the vector pseudotyped with Mokola-G (B), only the cells of the pigment epithelium (ep) are labeled.

5. Tropism of the Lentiviral Vectors Derived from HIV-1 and Pseudotyped with VSV- or Mokola-G, for Retinal Cells The lentiviral vectors derived from HIV-1 and pseudotyped with VSV- or Mokola-G were injected into the subretinal space of adult rats (rdy strain). For each pseudotype, various promoters allowing expression of the green fluorescent protein (GFP) reporter gene were tested: the CMV promoter (ubiquitous viral promoter), the PGK promoter (ubiquitous promoter of the mouse phosphoglycerate kinase gene) and the Rho promoter (2.2 kilobase fragment of the promoter of the gene for rhodopsin, a protein expressed specifically in retinal cells). One week and three weeks after injections, the GFP is detected in the live animal by angiography. At 4 weeks, the animal is sacrified and the GFP is visualized in two different ways: directly, on the flat-mounted retinal pigment epithelia, or by immunohistochemistry on thin sections of retina. These experiments made it possible to reveal the following results:

1. The two pseudotypes allow strong expression of GFP in the retina, which, with the CMV promoter is detectable in vivo by angiography (FIG. 4).
2. The two pseudotypes make it possible to transduce the cells of the pigment epithelium with great efficiency. Approximately a fourth to a third of the surface of the epithelium expresses GFP. In the transduced zone, 100% of the cells express GFP. This is clearly apparent on the flat-mounted pigment epithelia (FIG. 5).
3. By immunohistochemistry, GFP expression is detected in the photoreceptors after subretinal injection of the vectors pseudotyped with the VSV-G protein (FIG. 6a). This expression is greater with the specific Rho promoter than with the ubiquitous CMV and PGK promoters. On the other hand, after injection of the vectors pseudotyped with the Mokola-G protein, no GFP expression is detected in the photoreceptor layer, whatever the promoter used to control the GFP expression (FIG. 6b).

These experiments demonstrate that the lentiviral vectors derived from HIV-1 and pseudotyped with the Mokola G envelope make it possible to specifically transduce the cells of the retinal pigment epithelium subsequent to subretinal injection.

The invention claimed is:

1. A method for the transfer of a gene into the astrocytes of an individual comprising injecting into said individual, by direct injection, a composition comprising a defective lentivirus comprising said gene, said defective lentivirus being pseudotyped with a Mokola (MOK) envelope, so that said gene is transferred into the astrocytes of said individual.

2. The method of claims 1 wherein the gene is placed under the control of a transcriptional cytomegalovirus (CMV) promoter.

3. The method of claim 1, wherein the defective lentivirus comprises a lentiviral genome comprising a sequence LTR-Psi-RRE-flap-Promoter-Gene-LTR.

4. The method of claim 1, wherein the defective lentivirus is a virus of the HIV-1, HIV-2, SIV, FIV, EIAV, BIV, VISNA or CAEV type.

5. The method of claim 1 wherein said lentivirus is HIV-1 virus.

* * * * *